(12) United States Patent
Wu et al.

(10) Patent No.: US 8,287,969 B2
(45) Date of Patent: Oct. 16, 2012

(54) ISOSORBIDE DERIVATIVES AND LIQUID CRYSTAL DISPLAYS COMPRISING THE SAME

(75) Inventors: Chun-Ming Wu, Banqiao (TW); Kevin Lin, Taoyuan County (TW); Shih-Hsien Liu, Jhubei (TW); Chih-Lung Chin, Taoyuan County (TW); An-Cheng Chen, Hsinchu (TW); Kung-Lung Cheng, Hsinchu (TW); Chien-Hsien Cheng, Tainan (TW)

(73) Assignee: Industrial Technology Research Institute, Hsinchu County (TW)

( * ) Notice: Subject to any disclaimer, the term of this patent is extended or adjusted under 35 U.S.C. 154(b) by 155 days.

(21) Appl. No.: 12/968,294

(22) Filed: Dec. 15, 2010

(65) Prior Publication Data

US 2012/0086902 A1   Apr. 12, 2012

(30) Foreign Application Priority Data

Oct. 6, 2010   (TW) ................. 99133984 A

(51) Int. Cl.
| | |
|---|---|
| C09K 19/58 | (2006.01) |
| C09K 19/54 | (2006.01) |
| C07D 493/04 | (2006.01) |
| C07D 241/04 | (2006.01) |

(52) U.S. Cl. .............. 428/1.1; 252/299.2; 252/299.5; 544/336; 544/358; 544/377; 544/387; 544/389; 544/391; 544/392; 549/464

(58) Field of Classification Search .......... 252/299.5; 428/1.1; 544/336, 358, 377, 387, 389, 391, 544/392; 549/464
See application file for complete search history.

(56) References Cited

U.S. PATENT DOCUMENTS

| 5,139,698 | A | 8/1992 | Plach et al. |
| 6,022,969 | A * | 2/2000 | Rice et al. ............ 544/357 |
| 6,217,792 | B1 | 4/2001 | Parri et al. |
| 6,909,478 | B2 | 6/2005 | Ichihashi et al. |
| 7,112,290 | B2 | 9/2006 | Nakata et al. |
| 7,311,948 | B2 | 12/2007 | Lub et al. |
| 7,452,575 | B2 | 11/2008 | Francis et al. |
| 7,470,376 | B2 | 12/2008 | Welter et al. |
| 7,576,829 | B2 | 8/2009 | Kikuchi et al. |
| 7,630,029 | B2 | 12/2009 | Majumdar et al. |
| 7,704,568 | B2 | 4/2010 | Shukla et al. |
| 2007/0131901 | A1 | 6/2007 | Welter |

FOREIGN PATENT DOCUMENTS

| TW | 420763 | 2/2001 |
| TW | 201014862 A1 | 4/2010 |

* cited by examiner

*Primary Examiner* — Shean C Wu
(74) *Attorney, Agent, or Firm* — Pai Patent & Trademark Law Firm; Chao-Chang David Pai

(57) ABSTRACT

An isosorbide derivative of Formula (I) is provided.

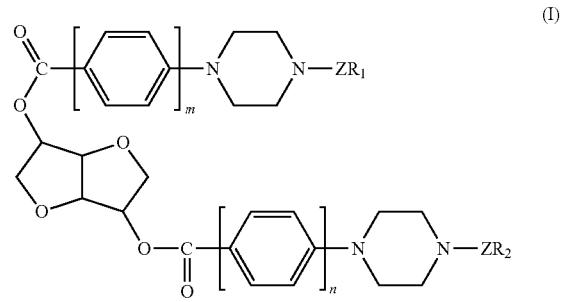

In Formula (I), Z is —$CH_2$—$CH_2$—, —CH=CH—, —C≡C—, —$CH_2$—O—, —$CH_2$—S—, —CH=N—O—, —CO—O—, —CO—S—, single bond, -ph-, —CO—O-ph- or —CO—O-ph-CO—O—, and ph represents benzene, $R_1$ and $R_2$ are, independently, C1-25 alkyl, —CN, —NCS, —$CX_3$ or —$OCX_3$, and X represents halogen, and m and n are, independently, 0, 1 or 2. The invention also provides a liquid crystal display including the isosorbide derivative.

4 Claims, No Drawings

ISOSORBIDE DERIVATIVES AND LIQUID CRYSTAL DISPLAYS COMPRISING THE SAME

CROSS REFERENCE TO RELATED APPLICATIONS

This Application claims priority of Taiwan Patent Application No. 99133984, filed on Oct. 6, 2010, the entirety of which is incorporated by reference herein.

BACKGROUND OF THE INVENTION

1. Field of the Invention

The invention relates to an isosorbide derivative, and more particularly to an isosorbide derivative doped into liquid crystal materials.

2. Description of the Related Art

Recently, along with the development of the liquid crystal industry, the applications of liquid crystal materials, for various requirements, have also grown. Cholesteric liquid crystals with bistability and stable frame performance under no applied voltage are popularly applied in new-generation flat panel display technology.

Cholesteric liquid crystal materials possess a helical structure and liquid crystal characteristics. The helical structure is normally formed by doping chiral dopants into achiral cholesteric liquid crystal molecules. Thus, the helical twist of the cholesteric liquid crystals is mainly determined by helical twisting power (HTP) of the chiral dopant. Generally, various chiral structures possess various HTP values.

A chiral dopant is an optically active substance. When a chiral dopant is added to liquid crystals with a nematic phase, the liquid crystals are twisted to form a cholesteric liquid crystal phase. The helical twisting power (HTP) of the chiral dopant is mainly determined by the characteristics thereof, which are simultaneously, affected by, for example, a nematic liquid crystal host and surrounding/process temperature.

BRIEF SUMMARY OF THE INVENTION

One embodiment of the invention provides an isosorbide derivative represented by Formula (I):

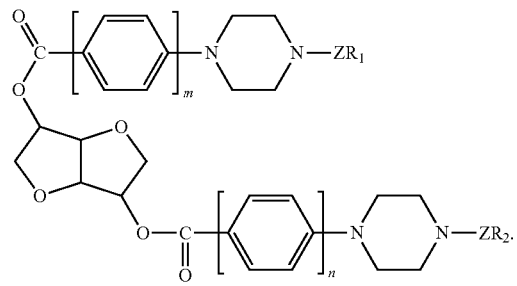

(I)

In Formula (I), Z is —$CH_2$—$CH_2$—, —CH=CH—, —C≡C—, —$CH_2$—O—, —$CH_2$—S—, —CH=N—O—, —CO—O—, —CO—S—, single bond, -ph-, —CO—O-ph- or —CO—O-ph-CO—O—, and ph represents benzene, $R_1$ and $R_2$ are, independently, C1-25 alkyl, —CN, —NCS, —$CX_3$ or —$OCX_3$, and X represents halogen, and m and n are, independently, 0, 1 or 2.

One embodiment of the invention provides a liquid crystal display comprising an upper substrate, a lower substrate opposed to the upper substrate, and a liquid crystal layer disposed between the upper substrate and the lower substrate, comprising an isosorbide derivative represented by Formula (I):

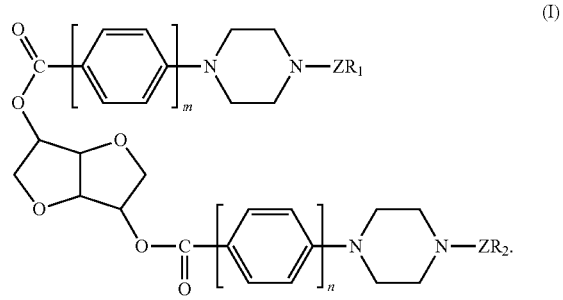

(I)

In Formula (I), Z is —$CH_2$—$CH_2$—, —CH=CH—, —C≡C—, —$CH_2$—O—, —$CH_2$—S—, —CH=N—O—, —CO—O—, —CO—S—, single bond, -ph-, —CO—O-ph- or —CO—O-ph-CO—O—, and ph represents benzene, $R_1$ and $R_2$ are, independently, C1-25 alkyl, —CN, —NCS, —$CX_3$ or —$OCX_3$, and X represents halogen, and m and n are, independently, 0, 1 or 2.

The invention provides a novel chiral dopant of isosorbide derivatives with a core structure of an isosorbide and a side chain containing piperazine. The disclosed isosorbide derivative effectively improves, for example, the temperature stability of cholesterol liquid crystals (for example achieving temperature dependence less than or equal to 0.2 nm/° C.). Additionally, the disclosed isosorbide derivative also possesses a large helical twisting power (HTP), for example exceeding 45 μm$^{-1}$, which considerably improves the helical twist of cholesterol liquid crystals.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides an isosorbide derivative represented by Formula (I):

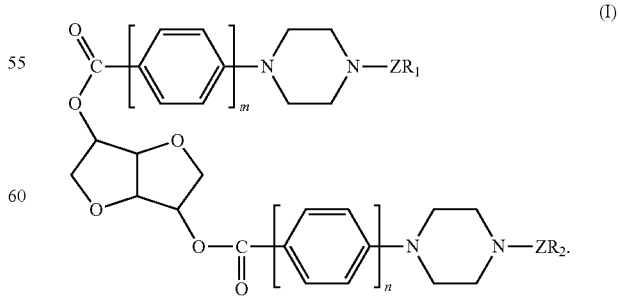

(I)

In Formula (I), Z may be —$CH_2$—$CH_2$—, —CH=CH—, —C≡C—, —$CH_2$—O—, —$CH_2$—S—, —CH=N—O—, —CO—O—, —CO—S—, single bond, -ph-, —CO—O-ph- or —CO—O-ph-CO—O—. The "ph" represents benzene.
R₁ and R₂ may be, independently, C1-25 alkyl, —CN, —NCS, —CX₃ or —OCX₃. The "X" represents halogen.
Additionally, m and n may be, independently, 0, 1 or 2.
Some exemplary isosorbide derivatives of the invention are disclosed as follows:
(Compound A-2C1)
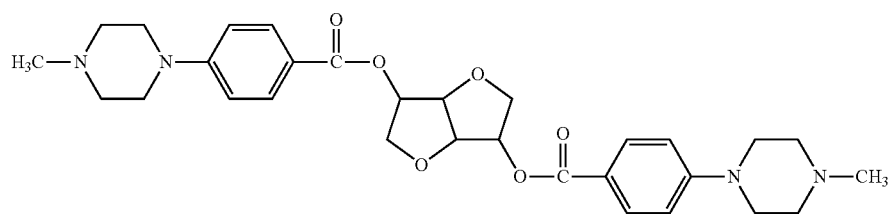
(Compound A-2C5)
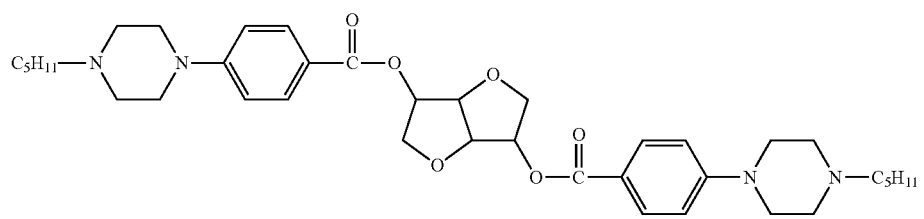
(Compound A-2IC5)
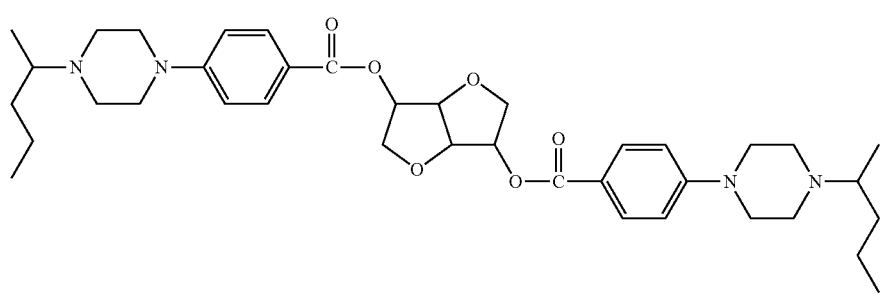
(Compound A-2BC5)
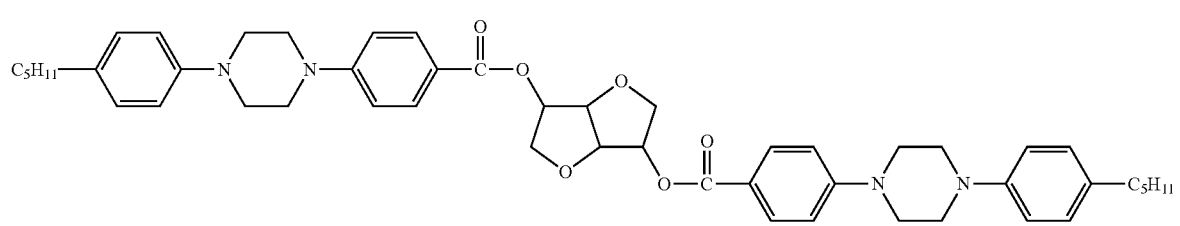
(Compound A-C1C5)
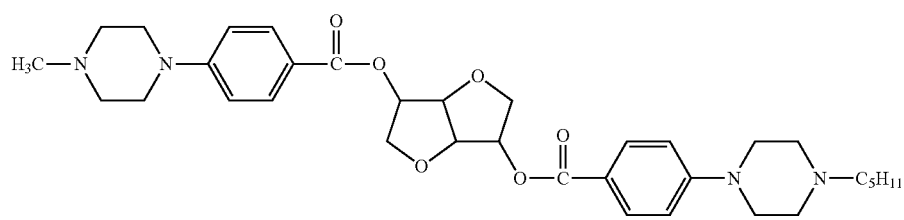
(Compound A-2aBC1)
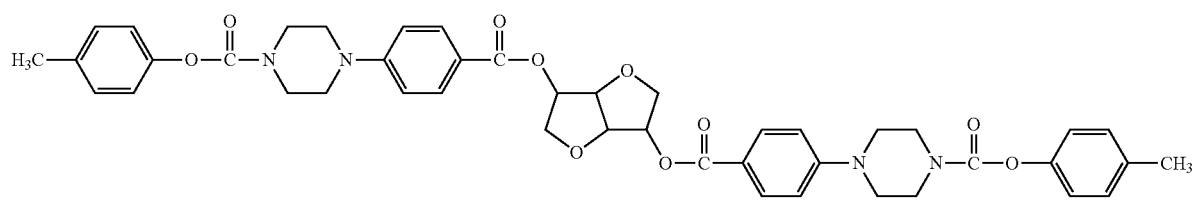

-continued

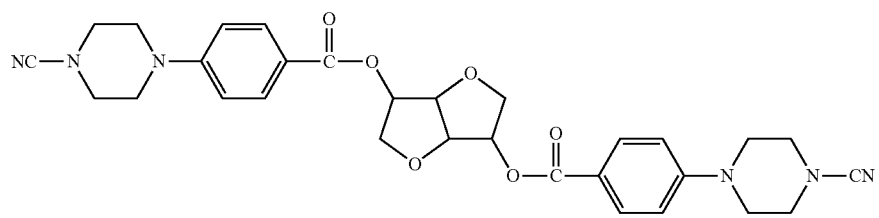
(Compound A-2CN)

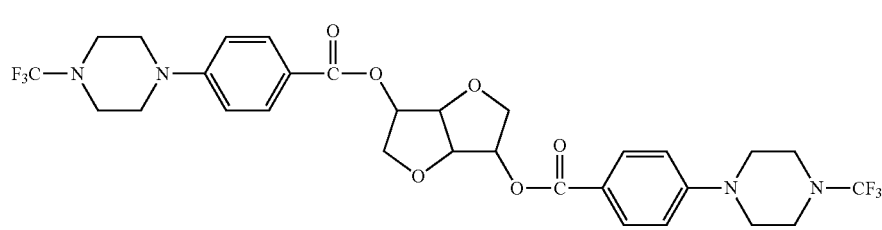
(Compound A-2CF3)

One embodiment of the invention provides a liquid crystal display comprising an upper substrate, a lower substrate opposed to the upper substrate, and a liquid crystal layer disposed between the upper substrate and the lower substrate, comprising an isosorbide derivative represented by Formula (I):

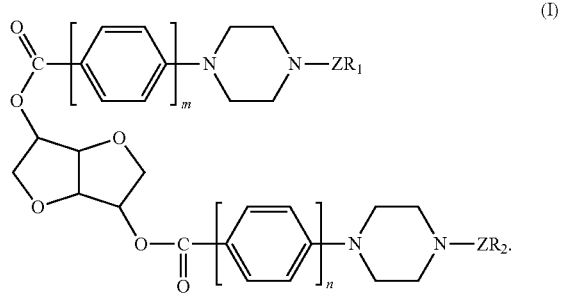
(I)

In Formula (I), Z may be —$CH_2$—$CH_2$—, —CH=CH—, —C≡C—, —$CH_2$—O—, —$CH_2$—S—, —CH=N—O—, —CO—O—, —CO—S—, single bond, -ph-, —CO—O-ph- or —CO—O-ph-CO—O—. The "ph" represents benzene.

$R_1$ and $R_2$ may be, independently, C1-25 alkyl, —CN, —NCS, —$CX_3$ or —$OCX_3$. The "X" represents halogen.

Additionally, m and n may be, independently, 0, 1 or 2.

The disclosed isosorbide derivative may be doped into, for example, a cholesterol liquid crystal display.

The invention provides a novel chiral dopant of isosorbide derivatives with a core structure of an isosorbide and a side chain containing piperazine. The disclosed isosorbide derivative effectively improves, for example, the temperature stability of cholesterol liquid crystals (for example achieving the temperature dependence less than or equal to 0.2 nm/° C.). Additionally, the disclosed isosorbide derivative also possesses a large helical twisting power (HTP), for example exceeding 45 µm$^{-1}$, which considerably improves helical twist of cholesterol liquid crystals.

EXAMPLE 1

Synthesis of an Isosorbide Derivative of the Invention I

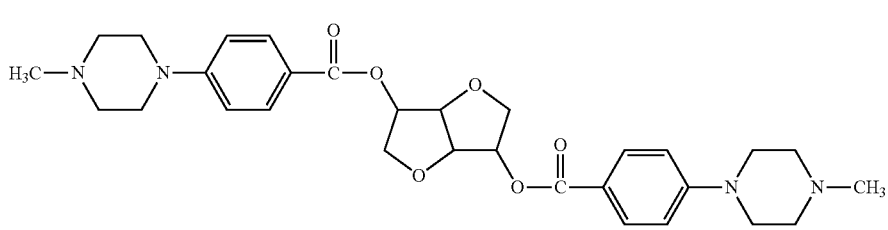
Compound A-2C1

First, 2.2 g of 4-[4-Methyl-piperazin-1-yl]-benzoic acid (10 mmol) and 2.43 g of 1,1"-Carbonyldiimidazole (CDI) (15 mmol) were placed in a 100 mL two-neck round-bottom flask. Next, 30 mL of anhydrous tetrahydrofuran (THF) was conducted into the flask under nitrogen. After reflux for 4 hours and cooling the flask to room temperature, "A" solution was prepared.

Next, 0.45 g of isosorbide (3 mmol) was placed in another round-bottom flask and then dissolved by adding THF under an ice bath. After adding NaH to the flask, "B" solution was prepared. After two hours, "A" solution was poured into "B" solution with stirring for about two hours to warm the flask to room temperature. After complete extraction, a yellow solid was obtained. The solid was then recrystallized with MeOH to form 1.15 g of a white solid of compound A-2C1 with a yield of 70%.

EXAMPLE 2

Synthesis of an Isosorbide Derivative of the Invention II

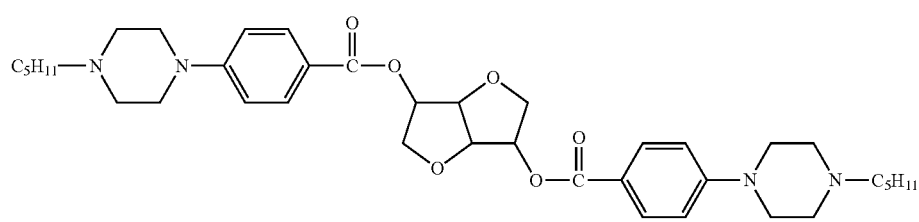

Compound A-2C5

First, 2.76 g of 4-[4-Pentyl-piperazin-1-yl]-benzoic acid (10 mmol) and 2.43 g of 1,1"-Carbonyldiimidazole (CDI) (15 mmol) were placed in a 100 mL two-neck round-bottom flask. Next, 30 mL of anhydrous tetrahydrofuran (THF) was conducted into the flask under nitrogen. After reflux for 4 hours and cooling the flask to room temperature, "A" solution was prepared.

Next, 0.45 g of isosorbide (3 mmol) was placed in another round-bottom flask and then dissolved by adding THF under an ice bath. After adding NaH to the flask, "B" solution was prepared. After two hours, "A" solution was poured into "B" solution with stirring for about two hours to warm the flask to room temperature. After complete extraction, a yellow solid was obtained. The solid was then recrystallized with MeOH to form 1.25 g of a white solid of compound A-2C5 with a yield of 63%.

EXAMPLE 3

Synthesis of an Isosorbide Derivative of the Invention III

First, 2.76 g of 4-[4-(1-Methyl-butyl)-piperazin-1-yl]-benzoic acid (10 mmol) and 2.43 g of 1,1"-Carbonyldiimidazole (CDI) (15 mmol) were placed in a 100 mL two-neck round-bottom flask. Next, 30 mL of anhydrous tetrahydrofuran (THF) was conducted into the flask under nitrogen. After reflux for 4 hours and cooling the flask to room temperature, "A" solution was prepared.

Next, 0.45 g of isosorbide (3 mmol) was placed in another round-bottom flask and then dissolved by adding THF under an ice bath. After adding NaH to the flask, "B" solution was prepared. After two hours, "A" solution was poured into "B" solution with stirring for about two hours to warm the flask to room temperature. After complete extraction, a yellow solid was obtained. The solid was then recrystallized with MeOH to form 1.29 g of a white solid of compound A-2IC5 with a yield of 65%.

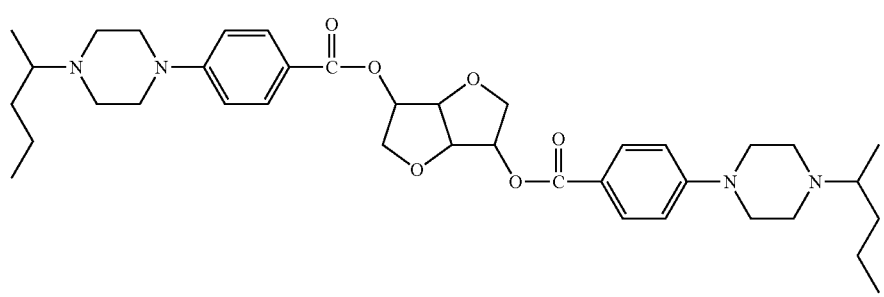

Compound A-2IC5

EXAMPLE 4

Synthesis of an Isosorbide Derivative of the Invention IV

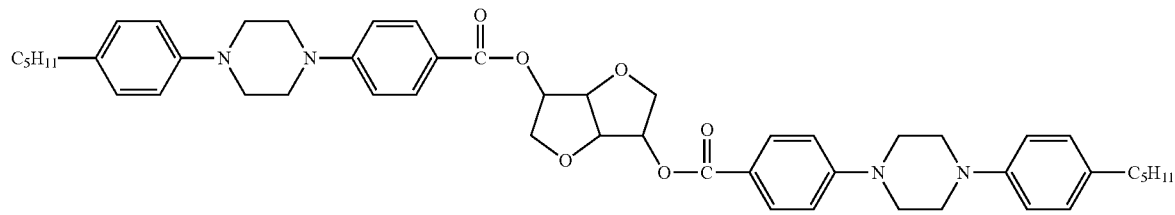

Compound A-2BC5

First, 3.52 g of 4-[4-(4-Pentyl-phenyl)-piperazin-1-yl]-benzoic acid (10 mmol) and 2.43 g of 1,1"-Carbonyldiimidazole (CDI) (15 mmol) were placed in a 100 mL two-neck round-bottom flask. Next, 30 mL of anhydrous tetrahydrofuran (THF) was conducted into the flask under nitrogen. After reflux for 4 hours and cooling the flask to room temperature, "A" solution was prepared.

Next, 0.45 g of isosorbide (3 mmol) was placed in another round-bottom flask and then dissolved by adding THF under an ice bath. After adding NaH to the flask, "B" solution was prepared. After two hours, "A" solution was poured into "B" solution with stirring for about two hours to warm the flask to room temperature. After complete extraction, a yellow solid was obtained. The solid was then recrystallized with MeOH to form 1.61 g of a white solid of compound A-2BC5 with a yield of 66%.

EXAMPLE 5

Synthesis of an Isosorbide Derivative of the Invention V

First, 2.2 g of 4-[4-Methyl-piperazin-1-yl]-benzoic acid (10 mmol) and 2.43 g of 1,1"-Carbonyldiimidazole (CDI) (15 mmol) were placed in a 100 mL two-neck round-bottom flask. Next, 30 mL of anhydrous tetrahydrofuran (THF) was conducted into the flask under nitrogen. After reflux for 4 hours and cooling the flask to room temperature, "A" solution was prepared.

Next, 1.9 g of isosorbide (13 mmol) was placed in another round-bottom flask and then dissolved by adding THF under an ice bath. After adding NaH to the flask, "B" solution was prepared. After two hours, "A" solution was poured into "B" solution with stirring for about two hours to warm the flask to room temperature. After complete extraction, a yellow solid was obtained. After column chromatography (eluent: ethyl acetate:hexane=1:1), 2.1 g of an intermediate (6 mmol) was formed with a yield of 66%.

Next, 2.21 g of 4-[4-Pentyl-piperazin-1-yl]-benzoic acid (8 mmol) and 2.43 g of 1,1"-Carbonyldiimidazole (CDI) (15 mmol) were placed in a 100 mL two-neck round-bottom flask. Next, 30 mL of anhydrous tetrahydrofuran (THF) was conducted into the flask under nitrogen. After reflux for 4 hours and cooling the flask to room temperature, "C" solution was prepared.

Next, the intermediate was placed in another round-bottom flask and then dissolved by adding THF under an ice bath. After adding NaH to the flask, "D" solution was prepared. After two hours, "C" solution was poured into "D" solution

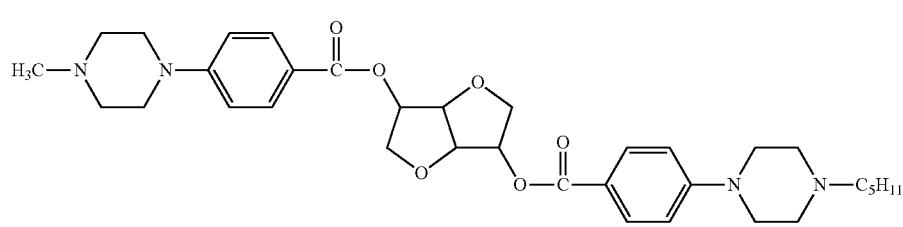

Compound A-C1C5 with stirring for about two hours to warm the flask to room temperature. After complete extraction, a yellow solid was obtained. The solid was then recrystallized with MeOH to form 1.83 g of a white solid of compound A-C1C5 with a yield of 50%.

EXAMPLE 6

Synthesis of an Isosorbide Derivative of the Invention VI

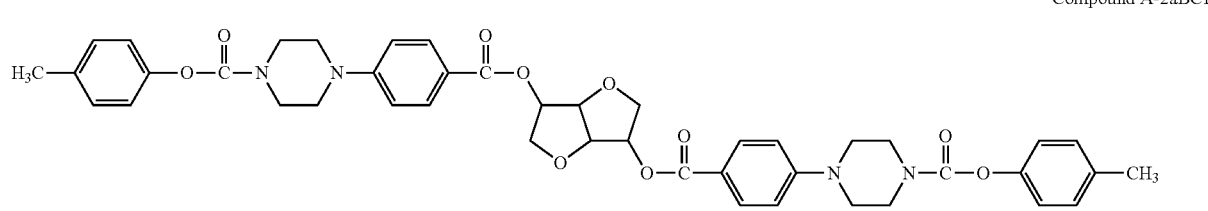

Compound A-2aBC1

First, 3.40 g of 4-(4-Carboxy-phenyl)-piperazin-1-carboxylic acid-p-tolyl ester (10 mmol) and 2.43 g of 1,1"-Carbonyldiimidazole (CDI) (15 mmol) were placed in a 100 mL two-neck round-bottom flask. Next, 30 mL of anhydrous tetrahydrofuran (THF) was conducted into the flask under nitrogen. After reflux for 4 hours and cooling the flask to room temperature, "A" solution was prepared.

Next, 0.45 g of isosorbide (3 mmol) was placed in another round-bottom flask and then dissolved by adding THF under an ice bath. After adding NaH to the flask, "B" solution was prepared. After two hours, "A" solution was poured into "B" solution with stirring for about two hours to warm the flask to room temperature. After complete extraction, a yellow solid was obtained. The solid was then recrystallized with MeOH to form 1.54 g of a white solid of compound A-2aBC1 with a yield of 65%.

EXAMPLE 7

Synthesis of an Isosorbide Derivative of the Invention VII

First, 2.31 g of 4-(4-cyano-piperazin-1-yl)-benzoic acid (10 mmol) and 2.43 g of 1,1"-Carbonyldiimidazole (CDI) (15 mmol) were placed in a 100 mL two-neck round-bottom flask. Next, 30 mL of anhydrous tetrahydrofuran (THF) was conducted into the flask under nitrogen. After reflux for 4 hours and cooling the flask to room temperature, "A" solution was prepared.

Next, 0.45 g of isosorbide (3 mmol) was placed in another round-bottom flask and then dissolved by adding THF under an ice bath. After adding NaH to the flask, "B" solution was prepared. After two hours, "A" solution was poured into "B" solution with stirring for about two hours to warm the flask to room temperature. After complete extraction, a yellow solid was obtained. The solid was then recrystallized with MeOH to form 0.9 g of a white solid of compound A-2CN with a yield of 68%.

Compound A-2CN

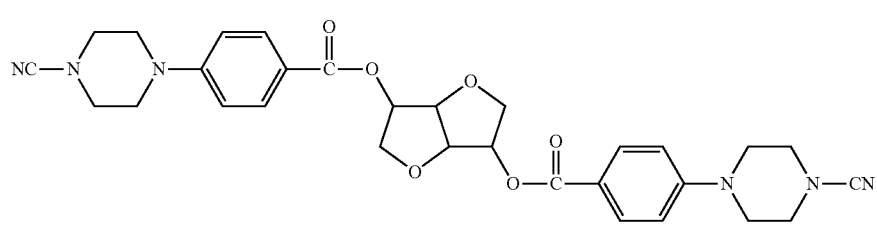

EXAMPLE 8

Synthesis of an Isosorbide Derivative of the Invention VIII

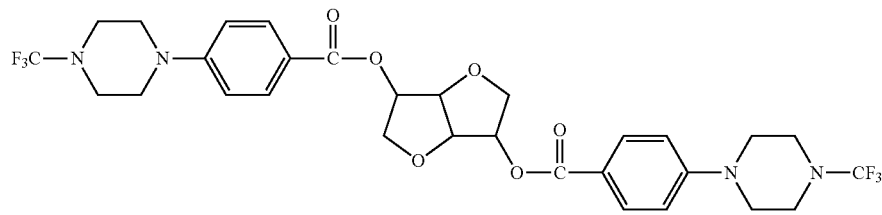

Compound A-2CF3

First, 2.74 g of 4-(4-Trifluoromethyl-piperazin-1-yl)-benzoic acid (10 mmol) and 2.43 g of 1,1"-Carbonyldiimidazole (CDI) (15 mmol) were placed in a 100 mL two-neck round-bottom flask. Next, 30 mL of anhydrous tetrahydrofuran (THF) was conducted into the flask under nitrogen. After reflux for 4 hours and cooling the flask to room temperature, "A" solution was prepared.

Next, 0.45 g of isosorbide (3 mmol) was placed in another round-bottom flask and then dissolved by adding THF under an ice bath. After adding NaH to the flask, "B" solution was prepared. After two hours, "A" solution was poured into "B" solution with stirring for about two hours to warm the flask to room temperature. After complete extraction, a yellow solid was obtained. The solid was then recrystallized with MeOH to form 1.18 g of a white solid of compound A-2CF3 with a yield of 60%.

EXAMPLE 9

Helical Twisting Power (HTP) and Temperature Dependence of the Isosorbide Derivatives of the Invention The related physical-chemical properties, for example helical twisting power (HTP) and temperature dependence ($d\lambda/dT$) of the isosorbide derivatives (compounds A-2C1, A-2C5, A-2I C5, A-2BC5, A-C1C5, A-2aBC1, A-2CN and A-2CF3) of the invention are shown in Table 1. The test temperature was 20-50° C.

TABLE 1

|  | A-2C1 | A-2C5 | A-2IC5 | A-2BC5 | A-C1C5 | A-2aBC1 | A-2CN | A-2CF3 |
|---|---|---|---|---|---|---|---|---|
| HTP ($\mu m^{-1}$) | 45 | 47 | 46 | 46 | 45 | 48 | 45 | 47 |
| $d\lambda/dT$ (nm/° C.) | +0.03 | −0.19 | −0.16 | −0.11 | −0.2 | −0.14 | −0.12 | −0.17 |

The results indicate that the disclosed isosorbide derivatives (compounds A-2C1, A-2C5, A-2IC5, A-2BC5, A-C1C5, A-2aBC1, A-2CN and A-2CF3) possess large helical twisting power (HTP), for example exceeding 45 $\mu m^{-1}$, and low temperature dependence, for example less than or equal to 0.2 nm/° C. Thus, the disclosed isosorbide derivative is considerably suitable for application in, for example, a cholesterol liquid crystal display.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An isosorbide derivative, represented by Formula (I):

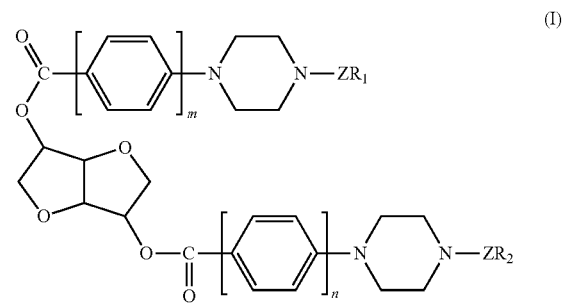

(I)

wherein

Z is —$CH_2$—$CH_2$—, —CH=CH—, —C≡C—, —$CH_2$—O—, —$CH_2$—S—, —CH=N—O—, —CO—O—, —CO—S—, single bond, -ph-, —CO—O-ph- or —CO—O-ph-CO—O—, and ph represents benzene;

$R_1$ and $R_2$ are, independently, C1-25 alkyl, —CN, —NCS, —$CX_3$ or —$OCX_3$, and X represents halogen; and m and n are, independently, 0, 1 or 2.

2. The isosorbide derivative as claimed in claim 1, wherein the isosorbide derivative comprises

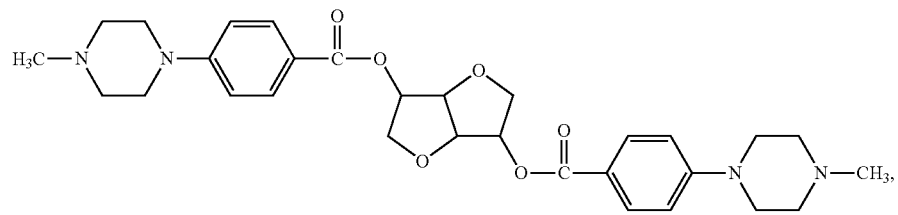
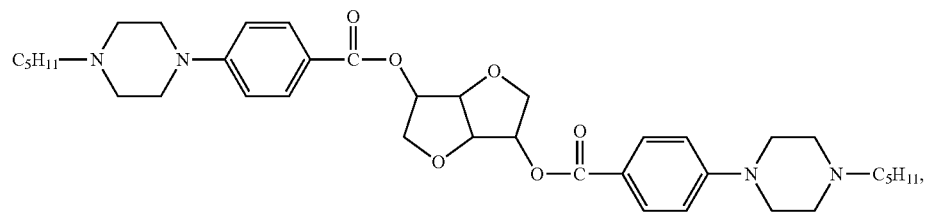
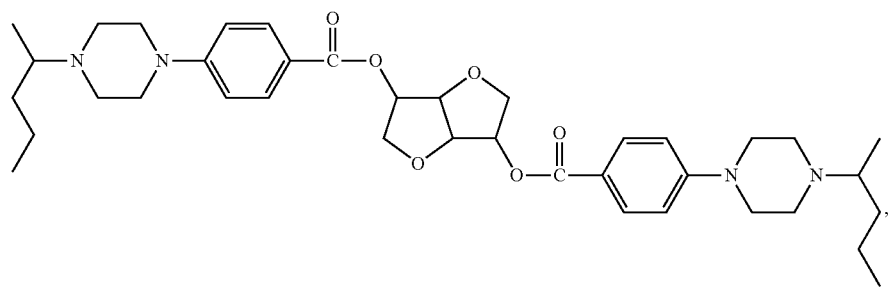
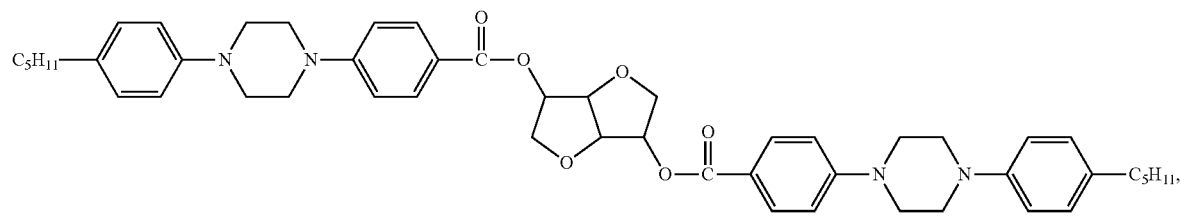
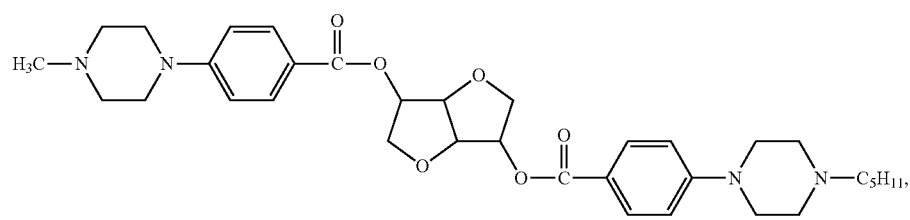
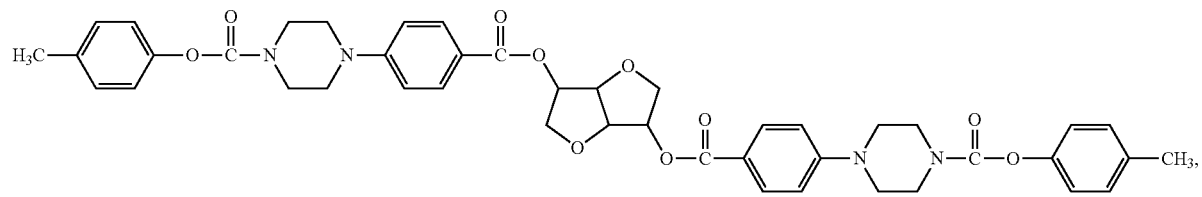
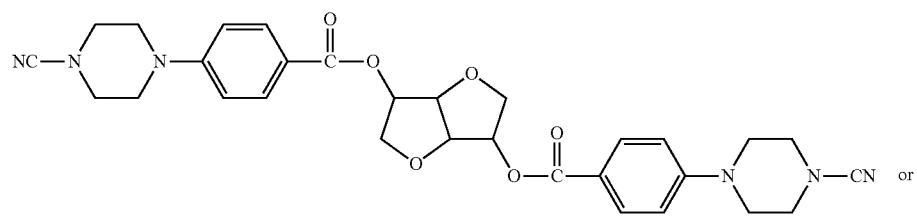

-continued

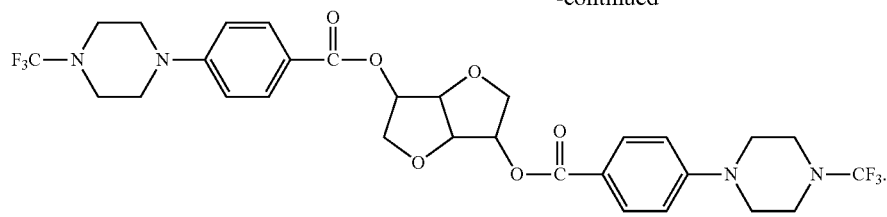

3. A liquid crystal display, comprising:
an upper substrate;
a lower substrate opposed to the upper substrate; and
a liquid crystal layer disposed between the upper substrate and the lower substrate, comprising an isosorbide derivative represented by Formula (I):

(I)

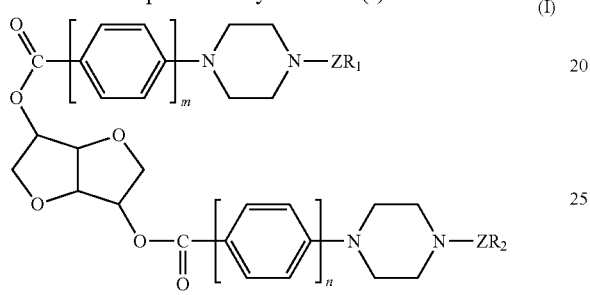

wherein Z is —$CH_2$—$CH_2$—, —CH═CH—, —C≡C—, —$CH_2$—O—, —$CH_2$—S—, —CH═N—O—, —CO—O—, —CO—S—, single bond, -ph-, —CO—O-ph- or —CO—O-ph-CO—O—, and ph represents benzene, $R_1$ and $R_2$ are, independently, C1-25 alkyl, —CN, —NCS, —$CX_3$ or —$OCX_3$, and X represents halogen, and m and n are, independently, 0, 1 or 2.

4. The liquid crystal display as claimed in claim 3, wherein the liquid crystal display is a cholesterol liquid crystal display.

\* \* \* \* \*